United States Patent
Asakura et al.

(10) Patent No.: US 9,809,837 B2
(45) Date of Patent: Nov. 7, 2017

(54) METHOD FOR EVALUATING SUITABILITY OF DUODENAL FLUID SAMPLE AS SAMPLE FOR DETECTING PANCREATIC FLUID-DERIVED COMPONENTS

(71) Applicant: OLYMPUS CORPORATION, Tokyo (JP)

(72) Inventors: Masanori Asakura, Kawasaki (JP); Tomonori Nagaoka, Tokyo (JP); Nao Shimada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/382,996

(22) Filed: Dec. 19, 2016

(65) Prior Publication Data
US 2017/0096699 A1    Apr. 6, 2017

Related U.S. Application Data

(63) Continuation of application No. PCT/JP2015/055403, filed on Feb. 25, 2015.

(51) Int. Cl.
C12Q 1/37 (2006.01)
G01N 33/58 (2006.01)

(52) U.S. Cl.
CPC ............ *C12Q 1/37* (2013.01); *G01N 33/582* (2013.01); *G01N 2333/96433* (2013.01); *G01N 2333/96477* (2013.01)

(58) Field of Classification Search
None
See application file for complete search history.

(56) References Cited

U.S. PATENT DOCUMENTS

| | | | |
|---|---|---|---|
| 6,441,131 B1 * | 8/2002 | Hayashi | C07K 5/0808 435/4 |
| 8,211,644 B2 | 7/2012 | Hanna et al. | |
| 2010/0028916 A1 * | 2/2010 | Ambar | C12Q 1/34 435/7.72 |
| 2014/0186863 A1 * | 7/2014 | Sanuki | G01N 33/574 435/7.92 |
| 2016/0116476 A1 * | 4/2016 | Takeichi | G01N 33/48 435/6.11 |

FOREIGN PATENT DOCUMENTS

| | | | |
|---|---|---|---|
| EP | 2757377 | * | 7/2014 |
| EP | 2757377 A1 | | 7/2014 |
| JP | 2000-503533 A | | 3/2000 |
| JP | 2008-506373 A | | 3/2008 |
| WO | WO 97/25437 A1 | | 7/1997 |
| WO | WO 2006/005622 | * | 1/2006 |
| WO | WO 2006/005622 A1 | | 1/2006 |
| WO | WO 2011/096515 A1 | | 8/2011 |
| WO | WO 2013/038981 A1 | | 3/2013 |
| WO | WO 2015/001831 A1 | | 1/2015 |

OTHER PUBLICATIONS

International Search Report dated May 26, 2015 issued in PCT/JP2015/055403.
Japanese Office Action dated May 24, 2016 issued in Japanese Patent Application No. 2016-504825.
Gueant, J. L. et al., "In-vitro test of haptocorrin degradation for biological diagnosis of exocrine pancreatic dysfunction using duodenal juice collected during endoscopy", The Lancet, 1986, pp. 709-712 vol. 2, No. 8509.
Mizuno, R. et al., "A Simple and Specific Determination of Duodenal Chymotrypsin and Its Diagnostic Value", Japanese Journal of Gastroenterology, 1982, pp. 858-863, vol. 79, No. 3.
Biochemistry Dictionary 3rd edition, 2002, p. 358 and p. 1262, Tokyo Kagaku Dojin Co., Ltd., with partial English translation.

* cited by examiner

*Primary Examiner* — Ralph Gitomer
(74) *Attorney, Agent, or Firm* — Scully, Scott, Murphy & Presser, P.C.

(57) ABSTRACT

A method is provided for evaluating the suitability of a duodenal fluid sample collected from an animal as a sample for detecting pancreatic fluid-derived components. The method includes: (a) mixing a duodenal fluid sample with a chymotrypsin-specific substrate and measuring an amount of degradation the chymotrypsin-specific substrate by of the duodenal fluid sample, (b) mixing the duodenal fluid sample with a pepsin-specific substrate and measuring an amount of degradation of the pepsin-specific substrate by the duodenal fluid sample, and (c) evaluating that the duodenal fluid sample is suitable as a sample for detecting pancreatic fluid-derived components if the amount of degradation of the chymotrypsin-specific substrate by the duodenal fluid sample is higher than a prescribed threshold value and the amount of degradation of the pepsin-specific substrate by the duodenal fluid sample is lower than a prescribed threshold value, as being suitable as a sample for detecting pancreatic fluid-derived components.

8 Claims, No Drawings

METHOD FOR EVALUATING SUITABILITY OF DUODENAL FLUID SAMPLE AS SAMPLE FOR DETECTING PANCREATIC FLUID-DERIVED COMPONENTS

BACKGROUND OF THE INVENTION

Field of the Invention

The present invention relates to a method for evaluating whether or not a duodenal fluid sample collected from an animal is suitable for detection of pancreatic fluid-derived components, or in other words, whether or not highly reliable results are obtained by using that duodenal fluid sample to detect pancreatic fluid-derived components.

The present application is a U.S. continuation application based on the PCT International Patent Application, PCT/JP2015/055403, filed on Feb. 25, 2015; the contents of which are incorporated herein by reference.

Description of the Related Art

Pancreatic fluid (body fluid discharged from the pancreatic duct) is an important biological sample for determining the status of the pancreas, and is used to test for pancreatic diseases using tests such as cytodiagnosis, bicarbonate measurement, bacteriological examinations, and tests for markers composed of proteins, nucleic acids and the like. In particular, analysis of cells and various biological components contained in pancreatic fluid can be expected to lead to early diagnosis of pancreatic cancer, for which early detection is difficult and which has an extremely poor prognosis.

Pancreatic fluid is typically collected endoscopically from the duodenal papilla by inserting a catheter into the pancreatic duct. However, this method has shortcomings such as being highly invasive for the patient and requiring the acquisition of a high degree of skill by the physician. Therefore, a method has been reported that consists of testing for pancreatic disease using duodenal fluid (body fluid collected from within the duodenum) instead of pancreatic fluid collected from the pancreatic duct (see, for example, PCT International Publication No. WO 2013/038981). Since pancreatic fluid is discharged from the pancreas into the duodenum, pancreatic disease can be tested by detecting pancreatic fluid components present in duodenal fluid. Duodenal fluid does not require an approach to the pancreatic duct during the collection step, and can be collected simply by inserting an endoscope into the duodenum and aspirating duodenal fluid directly. Namely, collection of duodenal fluid can be performed using a lowly invasive and simple procedure in comparison with collecting pancreatic fluid from the pancreatic duct.

In addition to pancreatic fluid discharged from the pancreas, duodenal fluid can contain bile produced in the liver and discharged via the gallbladder, mucus secreted in the duodenum, and gastric juice discharged from the stomach. In other words, duodenal fluid is a body fluid consisting of a mixture of pancreatic fluid, bile, mucus secreted in the duodenum and gastric juice, and the contents of each component vary. Consequently, it is unknown as to whether or not pancreatic fluid, which is considered to provide the most important information in terms of testing for pancreatic disease, is always present in duodenal fluid collected from a test subject. In the case of having collected multiple fractions from the same subject, there is thought to be deviations in the distribution of pancreatic fluid in those fractions, and pancreatic fluid is not necessarily contained in the collected duodenal fluid.

On the other hand, biological components such as proteins are susceptible to degradation and loss of activity. Consequently, in order to obtain highly reliable results, it is important to investigate the quality of biological samples. For example, Japanese Unexamined Patent Application, First Publication No. 2008-506373 discloses a screening method consisting of using a labeled peptide or protein provided with a site cleaved by protease as a standard, adding that standard to a biological sample and then monitoring changes in concentration over time in order to monitor changes and fluctuations in peptide or protein samples present in biological samples such as serum, plasma or whole blood.

SUMMARY OF THE INVENTION

As a result of conducting extensive studies to solve the aforementioned problems, the inventor of the present invention found that, a duodenal fluid sample having a high content of pancreatic fluid and a low content of gastric juice is suitable for detecting pancreatic fluid-derived components, and that the contents of pancreatic fluid and gastric juice present in duodenal fluid can be determined based on degradation activity on a substrate specific for chymotrypsin and a substrate specific for pepsin, respectively, thereby leading to completion of the present invention.

Namely, the method according to the present invention for evaluating the suitability of a duodenal fluid sample as a sample for detecting pancreatic fluid-derived components and the method for practicing collection of a duodenal fluid sample are as indicated in [1] to [10] below.

[1] A method for evaluating the suitability of a duodenal fluid sample as a sample for detecting pancreatic fluid-derived components, comprising:

(a) mixing a duodenal fluid sample with a chymotrypsin-specific substrate and measuring degradation activity of the duodenal fluid sample on the chymotrypsin-specific substrate, (b) mixing the duodenal fluid sample with a pepsin-specific substrate and measuring degradation activity of the duodenal fluid sample on the pepsin-specific substrate, and (c) evaluating whether or not the duodenal fluid sample is suitable as a sample for detecting pancreatic fluid-derived components based on the degradation activity of the duodenal fluid sample on the chymotrypsin-specific substrate and the degradation activity of the duodenal fluid sample on the pepsin-specific substrate.

[2] The method for evaluating the suitability of a duodenal fluid sample as a sample for detecting pancreatic fluid-derived components described in [1] above, wherein a site in the chymotrypsin-specific substrate cleaved by chymotrypsin is a structure represented by the following general formula (1):

[Chemical Formula 1]

(wherein, $Y^1$ and $Y^2$ respectively and independently represent an amino acid residue or $-CH_2-NH-$, $X^1$ represents Phe, Trp or Tyr, and $n^1$ and $n^2$ respectively and independently represent an integer of 1 to 10), and a site in the pepsin-specific substrate cleaved by pepsin is a structure represented by the following general formula (2):

[Chemical Formula 2]

(wherein, $Y^3$ and $Y^4$ respectively and independently represent an amino acid residue or $-CH_2-NH-$, $X^2$ represents Phe, Trp or Tyr, and $n^3$ and $n^4$ respectively and independently represent an integer of 1 to 10).

[3] The method for evaluating the suitability of a duodenal fluid sample as a sample for detecting pancreatic fluid-derived components described in [1] or [2] above, wherein the chymotrypsin-specific substrate and the pepsin-specific substrate are labeled with mutually the same or different types of labeling substances.

[4] The method for evaluating the suitability of a duodenal fluid sample as a sample for detecting pancreatic fluid-derived components described in [3] above, wherein the degradation activity of the chymotrypsin-specific substrate is determined based on the amount of degradation product of the chymotrypsin-specific substrate, the degradation activity of the pepsin-specific substrate is determined based on the amount of degradation product of the pepsin-specific substrate, and the amount of degradation product of the chymotrypsin-specific substrate and the amount of degradation product of the pepsin-specific substrate are determined by using the labeling substance as an indicator.

[5] The method for evaluating the suitability of a duodenal fluid sample as a sample for detecting pancreatic fluid-derived components described in [3] or [4] above, wherein the labeling substance is a fluorescent substance.

[6] The method for evaluating the suitability of a duodenal fluid sample as a sample for detecting pancreatic fluid-derived components described in [1] above, wherein the degradation activity of the chymotrypsin-specific substrate is determined based on the chymotrypsin content of the duodenal fluid sample, and the degradation activity of the pepsin-specific substrate is determined based on the pepsin content of the duodenal fluid sample.

[7] The method for evaluating the suitability of a duodenal fluid sample as a sample for detecting pancreatic fluid-derived components described in any of [1] to [6] above, wherein the operations (a) and (b) are respectively carried out on a plurality of duodenal fluid samples collected from two or more different sites of the digestive tract of the same subject, and the operation (c) comprises:

(c') evaluating a duodenal fluid sample among the plurality of duodenal fluid samples, in which degradation activity on the chymotrypsin-specific substrate is high and degradation activity on the pepsin-specific substrate is low, as being suitable as a sample for detecting pancreatic fluid-derived components.

[8] A method for practicing collection of a duodenal fluid sample that is suitable as a sample for detecting pancreatic fluid-derived components using a digestive tract simulator; wherein, the digestive tract simulator is at least provided with a simulated mouth, a simulated esophagus, a simulated stomach injected with simulated gastric juice, and a simulated duodenum injected with simulated pancreatic fluid through a simulated papilla, the simulated gastric juice is a solution containing pepsin and having a pH of 1 to 2, the simulated pancreatic fluid is a solution containing chymotrypsin and having a pH of 8 to 9, the following operations (1) and (2) are carried out once or repeated two or more times, and in the following operation (1), practice is carried out so as to be able to collect a duodenal fluid sample for which the degradation activity on a chymotrypsin-specific substrate is higher than a prescribed threshold value and the degradation activity on a pepsin-specific substrate is lower than a prescribed threshold value:

(1) collecting a simulated duodenal fluid sample from one or two or more different sites of the simulated duodenum by inserting an endoscope equipped with an internal catheter for collecting body fluid from the simulated mouth to the simulated duodenum of the digestive tract simulator; and, (2) measuring each of the simulated duodenal fluid samples collected in (1) for degradation activity on the chymotrypsin-specific substrate and degradation activity on the pepsin-specific substrate, respectively.

[9] The method for practicing collection of a duodenal fluid sample described in [8] above, wherein a site in the chymotrypsin-specific substrate cleaved by chymotrypsin is a structure represented by the following general formula (1):

[Chemical Formula 3]

  (1)

(wherein, $Y^1$ and $Y^2$ respectively and independently represent an amino acid residue or —$CH_2$—$NH$—, $X^1$ represents Phe, Trp or Tyr, and $n^1$ and $n^2$ respectively and independently represent an integer of 1 to 10), and a site in the pepsin-specific substrate cleaved by pepsin is a structure represented by the following general formula (2):

[Chemical Formula 4]

  (2)

(wherein, $Y^3$ and $Y^4$ respectively and independently represent an amino acid residue or —$CH_2$—$NH$—, $X^2$ represents Phe, Trp or Tyr, and $n^3$ and $n^4$ respectively and independently represent an integer of 1 to 10).

[10] The method for practicing collection of a duodenal fluid sample described in [8] or [9] above, wherein the chymotrypsin-specific substrate and the pepsin-specific substrate are labeled with mutually the same or different types of labeling substances, the degradation activity on the chymotrypsin-specific substrate is determined based on the amount of degradation product of the chymotrypsin-specific substrate, the degradation activity on the pepsin-specific substrate is determined based on the amount of degradation product of the pepsin-specific substrate, and the amount of degradation product of the chymotrypsin-specific substrate and the amount of degradation product of the pepsin-specific substrate are determined by using the labeling substance as an indicator.

DETAILED DESCRIPTION OF THE PREFERRED EMBODIMENTS

<Method for Evaluating Suitability of Duodenal Fluid Sample as Sample for Detecting Pancreatic Fluid-Derived Components>

The method for evaluating the suitability of a duodenal fluid sample as a sample for detecting pancreatic fluid-derived components of the present invention (to be referred to as the "method for evaluating suitability according to the present invention") comprises the following operations (a) to (c):

(a) mixing a duodenal fluid sample and a chymotrypsin-specific substrate and measuring degradation activity of the duodenal fluid sample on the chymotrypsin-specific substrate, (b) mixing the duodenal fluid sample with a pepsin-specific substrate and measuring degradation activity of the duodenal fluid sample on the pepsin-specific substrate, and (c) evaluating whether or not the duodenal fluid sample is suitable as a sample for detecting pancreatic fluid-derived components based on degradation activity of the duodenal fluid sample on the chymotrypsin-specific substrate and degradation activity of the duodenal fluid sample on the pepsin-specific substrate.

In the case of using a duodenal fluid sample having a low content of pancreatic fluid or not containing pancreatic fluid in testing, even if a target pancreatic disease marker is contained in the pancreatic fluid, that pancreatic disease marker would not be detected during testing resulting in a false negative. In addition, in the case a duodenal fluid sample is highly contaminated with gastric juice, pancreatic fluid-derived components present in the duodenal fluid sample may be degraded, modified or deactivated by the acidic pH or various proteases originating in the gastric juice. Consequently, in the case of using a duodenal fluid sample highly contaminated by gastric juice in testing, even if the sample contains pancreatic fluid, there is a high likelihood of the testing yielding a false negative result. In other words, in the case of testing for pancreatic fluid-derived components using a duodenal fluid sample, it is necessary that pancreatic fluid is contained in the duodenal fluid sample used in testing and that the duodenal fluid sample contains little gastric juice in order to obtain reliable test results.

Therefore, in the method for evaluating suitability according to the present invention, whether or not a duodenal fluid sample collected from an animal is suitable as a sample for detecting pancreatic fluid-derived components is evaluated by using the content of pancreatic fluid and the content of gastric juice as indicators. A duodenal fluid sample having a high pancreatic fluid content and low gastric juice content is evaluated as having high suitability as a sample for detecting pancreatic fluid-derived components (to also be simply referred to as having high "sample suitability"), while a duodenal fluid sample having a low pancreatic fluid content and high gastric juice content is evaluated as having low sample suitability.

In the present invention, the contents of pancreatic fluid and gastric juice in a duodenal fluid sample are investigated based on the degradation activity thereof on a substrate specific for chymotrypsin and a substrate specific for pepsin, respectively. Although digestive juices are organ specific and pancreatic fluid and gastric juice each contain various digestive enzymes, the major digestive enzymes of pancreatic fluid are chymotrypsin and trypsin, while the major digestive enzyme of gastric juice is pepsin. In other words, a duodenal fluid sample having a high level of degradation activity on a chymotrypsin-specific substrate is presumed to have a high content of chymotrypsin and therefore a high content of pancreatic fluid. A duodenal fluid sample having a high level of degradation activity on a pepsin-specific substrate is presumed to have a high content of pepsin and therefore a high content of gastric juice.

Chymotrypsin is a type of serine protease that exhibits peak activity at pH 8. Chymotrypsin cleaves the C-terminal side of a phenylalanine residue (Phe), tryptophan residue (Trp) or tyrosine residue (Tyr) not located after a proline residue (Pro) in a peptide. Trypsin is a type of serine protease that exhibits peak activity at pH 5 to 6. Trypsin cleaves the C-terminal of an arginine residue (Arg) or lysine residue (Lys) not located after a proline residue in a peptide. Pepsin is an acidic protease that exhibits peak activity at pH 2. Pepsin cleaves the N-terminal side of a leucine residue (Leu), phenylalanine residue, tryptophan residue or tyrosine residue not located before a proline residue in a peptide.

Since gastric juice is acidic, a duodenal fluid sample having low pH can be said to have high gastric juice content. In other words, the pH of a duodenal fluid sample can serve as an indicator of gastric juice content. However, since bile, which has a buffering action, is also contained in duodenal fluid samples, a pH of a duodenal fluid sample being low does not necessarily mean that the sample does not contain gastric juice. In this manner, in addition to having low sensitivity with respect to the use of gastric juice content as an indicator, the pH of a duodenal fluid sample is also affected by bile content. In addition, pH cannot be used as an indicator of gastric juice contamination when a collected duodenal fluid sample is immediately mixed with a buffer or preservative. In the present invention, since degradation activity on a pepsin-specific substrate is used as an indicator of gastric juice content, the presence or absence of contamination by gastric juice can be determined with higher sensitivity than in the case of using pH as an indicator.

In the method for evaluating suitability according to the present invention, degradation activity of an evaluation target in the form of a duodenal fluid sample on a chymotrypsin-specific substrate is measured in operation (a). The degradation activity on the chymotrypsin-specific substrate is determined based on the amount of degradation product of the chymotrypsin-specific substrate. Namely, the greater the amount of degradation product of the chymotrypsin-specific substrate, the higher the degradation activity of the duodenal fluid sample on the chymotrypsin-specific substrate. More specifically, after having mixed a chymotrypsin-specific substrate into a duodenal fluid sample and incubating for a prescribed period of time to carry out an enzymatic reaction, the amount of degradation product of the chymotrypsin-specific substrate is measured. Furthermore, in this operation, only one type or two or more types of chymotrypsin-specific substrates may be mixed into the duodenal fluid sample.

In the method for evaluating suitability according to the present invention, degradation activity of an evaluation target in the form of a duodenal fluid sample on a pepsin-specific substrate is measured in operation (b). The degradation activity on the pepsin-specific substrate is determined based on the amount of degradation product of the pepsin-specific substrate. Namely, the greater the amount of degradation product of the pepsin-specific substrate, the higher the degradation activity of a duodenal fluid sample on the pepsin-specific substrate. More specifically, after having mixed a pepsin-specific substrate into a duodenal fluid sample and incubating for a prescribed period of time to carry out an enzymatic reaction, the amount of degradation product of the pepsin-specific substrate is measured. Furthermore, in this operation, only one type or two or more types of pepsin-specific substrates may be mixed into the duodenal fluid sample.

There are no particular limitations on the chymotrypsin-specific substrate used in the present invention provided it is a substance which, although degraded by chymotrypsin, is not degraded by digestive enzymes contained in gastric juice, and although a substance that is only degraded by chymotrypsin is preferable, it may also be a substance that is degraded by enzymes not contained in gastric juices in addition to chymotrypsin. Similarly, there are no particular limitations on the pepsin-specific substrate used in the present invention provided it is a substance which, although degraded by pepsin, is not degraded by digestive enzymes contained in pancreatic fluid, and although a substance that is only degraded by pepsin is preferable, it may also be a substance that is degraded by enzymes not contained in pancreatic fluid in addition to pepsin.

A substance in which the site recognized and cleaved by chymotrypsin (chymotrypsin recognition site) is a structure represented by the following general formula (1) is preferable for the chymotrypsin-specific substrate used in the present invention. As a result of the chymotrypsin recognition site being a structure represented by the following general formula (1), the site is not cleaved by digestive enzymes contained in gastric juice, including pepsin, but rather is specifically cleaved by chymotrypsin. In the following general formula (1), $Y^1$ and $Y^2$ respectively and independently represent an amino acid residue or —$CH_2$—NH—, $X^1$ represents Phe, Trp or Tyr, and $n^1$ and $n^2$ respectively and independently represent an integer of 1 to 10.

[Chemical Formula 5]

$$—(Y^1)n^1\text{-}(X^1)\text{-Pro-}(Y^2)n^2- \quad (1)$$

The chymotrypsin-specific substrate used in the present invention may be a substance composed only of a chymotrypsin recognition site, or a substance also containing a domain other than the chymotrypsin recognition site. A domain in the chymotrypsin-specific substrate other than the chymotrypsin recognition site is required to be composed of a structure that is not degraded by digestive enzymes contained in gastric juice, including pepsin. For example, in the case the chymotrypsin recognition site is a structure represented by the aforementioned general formula (1), the chymotrypsin-specific substrate may be a substance in which both ends of a structure represented by the general formula (1) are bound to hydrogen atoms, or a substance in which either end of a structure represented by the general formula (1) is bound to a structure other than a hydrogen atom that is not degraded by digestive enzymes contained in gastric juice.

A substance in which the site recognized and cleaved by pepsin (pepsin recognition site) is a structure represented by the following general formula (2) is preferable for the pepsin-specific substrate used in the present invention. As a result of the pepsin recognition site being a structure represented by the following general formula (2), the site is not cleaved by digestive enzymes contained in pancreatic fluid, including chymotrypsin, but rather is specifically cleaved by pepsin. In the following general formula (2), $Y^3$ and $Y^4$ respectively and independently represent an amino acid residue or —$CH_2$—NH—, $X^2$ represents Phe, Trp or Tyr, and $n^3$ and $n^4$ respectively and independently represent an integer of 1 to 10.

[Chemical Formula 6]

$$—(Y^3)n^3\text{-Pro-}(X^2)—(Y^4)n^4- \quad (2)$$

In general formula (1), $n^1$ and $n^2$ respectively and independently may represent an integer of 1 to 5 or an integer of 1 to 3. In general formula (2), $n^3$ and $n^4$ respectively and independently may represent an integer of 1 to 5 or an integer of 1 to 3.

In the case $Y^1$ and $Y^2$ in general formula (1) and $Y^3$ and $Y^4$ in general formula (2) are amino acid residues, there are no particular limitations on those amino acid residues, and they may be any of the 20 types of so-called naturally-occurring amino acid residues (including proline) encoded by animal genes, or may be non-naturally-occurring amino acid residues. In addition, in the case of an amino acid residue having optical isomers, the amino acid residue may be in the D-form or L-form. An amino acid residue having a polar side chain is preferable as a naturally-occurring amino acid residue so that a substance in which a chymotrypsin recognition site or pepsin recognition site is represented by general formula (1) or general formula (2), respectively, has sufficient solubility in an aqueous solvent, and among these, a basic amino acid residue such as a lysine residue, histidine residue or arginine residue is more preferable, and a lysine residue or arginine residue is even more preferable from the viewpoint of structural stability. Examples of non-naturally-occurring amino acid residues include epsilon-aminocaproic acid ($\epsilon$-Acp), hydroxylysine, pyrrolysine, acetyllysine and ethylalanine, and $\epsilon$-Acp is preferable. Furthermore, in the case $n^1$ is an integer of 2 or more, the plurality of $Y^1$ present in a single molecule may all be of the same type or different types. In the case $n^2$, $n^3$ and $n^4$ represent integers of 2 or more as well, the plurality of $Y^2$, $Y^3$ and $Y^4$ present in a single molecule may similarly all be of the same type or different types.

A substance in which the chymotrypsin recognition site is a structure represented by general formula (1) may be a substance in which $Y^1$ is $\epsilon$-Asp, $Y^2$ is a basic amino acid residue and $n^1$ and $n^2$ are respectively and independently an integer of 1 to 3 (provided that, in the case $n^2$ is 2 or 3, the plurality of $Y^2$ may be the same type of amino acid residues or mutually different types of amino acid residues). Similarly, a substance in which the pepsin recognition site is a structure represented by general formula (2) may be a substance in which $Y^3$ is $\epsilon$-Asp, $Y^4$ is a basic amino acid residue and $n^3$ and $n^4$ are respectively and independently an integer of 1 to 3 (provided that, in the case $n^4$ is 2 or 3, the plurality of $Y^4$ may be the same type of amino acid residues or mutually different types of amino acid residues).

The peptide-specific substrate used in the present invention may be a substance composed only of a pepsin recognition site or a substance also containing a domain other than a pepsin recognition site. A domain in the pepsin-specific substrate other than the pepsin recognition site is required to be composed of a structure that is not degraded by digestive enzymes contained in pancreatic fluid, including chymotrypsin. For example, in the case the pepsin recognition site is a structure represented by the aforementioned general formula (2), the pepsin-specific substrate may be a substance in which both ends of a structure represented by the general formula (2) are bound to hydrogen atoms, or a substance in which either end of a structure represented by the general formula (2) is bound to a structure other than a hydrogen atom that is not degraded by digestive enzymes contained in pancreatic fluid.

The chymotrypsin-specific substrate used in the present invention may be labeled with one type or two or more types of labeling substances so as to be able to be detected while distinguishing between substances degraded by chymotrypsin and substances not degraded by chymotrypsin. Similarly, the pepsin-specific substrate used in the present invention may be labeled with one type or two or more types of labeling substance so as to be able to be detected while distinguishing between substances degraded by pepsin and substances not degraded by pepsin. A labeling substance can be used that is suitably selected from among labeling substances typically used to label peptides and other biological molecules. The labeling substance used to label the chymotrypsin-specific substrate and the labeling substance used to label the pepsin-specific substrate may be of the same type or different types. Examples of such labeling substances include luminescent substances, magnetic particles, radioisotopes, non-radioisotopes, isobars, nucleic acids, peptide tags and low molecular weight compounds. Although the luminescent substance is typically a fluorescent substance, it may also be a substance that emits light by phosphorescence, chemiluminescence, bioluminescence or light scattering. At least a fluorescent substance may be used for the labeling substance from the viewpoints of high sensitivity and high degree of safety.

There are no particular limitations on the fluorescent substance used as a labeling substance of the chymotrypsin-specific substrate and the like provided it is a substance that emits fluorescent light as a result of radiating light of a specific wavelength, and can be used by suitably selecting from among fluorescent substances, quantum dots and the like ordinarily used to label proteins, nucleic acids and the like. Specific examples of fluorescent substances include fluorescein isothiocyanate (FITC), fluorescein, rhodamine, TAMRA, NBD, tetramethylrhodamine (TMR), 2-(N-methylamino) benzoyl (Nma, ex: 340 nm/em: 440 nm), members of the CAL Fluor™ series (Biosearch Technologies), members of the Cy™ series (GE Healthcare Bio-Sciences), members of the HiLyte Fluor™ series (AnaSpec), members of the Alexa Fluor™ series (Invitrogen), members of the ATTO™ dye series (ATTO-TEC), 2,4-dinitrophenol (Dnp) and BHQ2C. Examples of quantum dots include CdSe.

The amount of degradation products of the chymotrypsin-specific substrate and pepsin-specific substrate used in the present invention (to also be collectively referred to as the "protease substrates used in the present invention") can be determined by using a labeling substance as an indicator. Various methods can be used for the method used to measure these degradation products corresponding to the labeling substance used to label each substrate. Examples of measurement methods include measurement of fluorescence intensity, measurement of changes in the amount of transmitted light relative to light of a specific wavelength using a spectrophotometer, measurement of light emission, measurement of radioactivity, microscopic methods, immunological methods, molecular biological methods, mass spectrometry, surface-enhanced laser desorption/ionization (SELDI), nuclear magnetic resonance and plasmon resonance.

For example, in the case the amount of a protease substrate prior to degradation and the amount of a degradation product following degradation are sufficiently different, the amount of the degraded protease substrate is measured by using a method consisting of detecting that amount by distinguishing according to the size of those amounts. In this detection method, for example, a degradation product isolated from a non-degraded protease substrate by applying a reaction solution to SDS-PAGE following incubation thereof can be detected by CBB staining or silver staining and the like. The amount of degradation product is determined according to staining intensity. In addition, the amount of a degradation product can also be determined from the chromatographic peak of a degradation product isolated from a non-degraded protease substrate by applying a reaction solution to high-performance liquid chromatography (HPLC) following incubation thereof.

In addition, a degradation product of a protease substrate can be detected while distinguishing from a non-degraded protease substrate by using fluorescence resonance energy transfer (FRET) using a complex, obtained by binding a donor in the form of a fluorescent substance and an acceptor in the form of a quenching substance so as to interpose a protease recognition site, as a protease substrate. In this case, although there is hardly any generation of fluorescence attributable to FRET by the non-degraded protease substrate, when a protease recognition site is cleaved by protease, distance between the fluorescent substance and quenching substance increases, FRET no long occurs and fluorescence from the fluorescent substance is intensely detected. Namely, the amount of degraded protease substrate is expressed by the amount of fluorescent substance emitting fluorescent light in the reaction solution following incubation.

In addition, a degradation product of a protease substrate can be detected while distinguishing from a non-degraded protease substrate by using solid-liquid separation treatment and using a solid-phase support, which uses a complex obtained by binding a solid-phase support or substance capable of binding directly or indirectly to a solid-phase support (referred to as a "linker") to a fluorescent substance, so as to interpose a protease recognition site as the protease substrate. Although the fluorescent substance derived from the non-degraded protease substrate binds directly or indirectly to the solid-phase support, the fluorescent substance derived from the protease substrate degraded by protease separates from the solid-phase support. Consequently, when solid-liquid separation treatment is carried out after having incubated a mixture of protease substrate and duodenal fluid sample (reaction liquid), the fluorescent substance derived from the non-degraded protease substrate is separated together with the solid-phase support, and the fluorescent substance derived from the degraded protease substrate is recovered in the liquid phase. In other words, the amount of degradation product of the protease substrate is expressed by the amount of fluorescent substance in the liquid phase. In the case the protease substrate is bound to the solid-phase support through a linker substance, the solid-phase support may be incubated with the protease substrate after adding to a duodenal fluid sample, or the protease support and duodenal fluid sample may be incubated followed by contacting the reaction solution with the solid-phase support following incubation.

There are no particular limitations on the shape or material of the solid-phase support provided it is a solid provided with a protease recognition site or site that binds directly or indirectly to a linker substance. For example, the solid-phase support may be in the form of particles, such as beads capable of being suspended in water and able to be separated from a liquid by ordinary solid-liquid separation treatment, a membrane, or a container or chip substrate. Specific examples of the solid-phase support include magnetic beads, silica beads, agarose gel beads, polyacrylamide resin beads, latex beads, polystyrene and other plastic beads, ceramic beads, zirconia beads, silica membranes, silica filters and plastic plates.

Examples of linker substances include biotin, avidin, streptavidin, glutathione, Dnp, digoxigenin, digoxin, polysaccharides composed of two or more sugars, polypeptides composed of four or more amino acids such as His tag, Flag tag or Myc tag, auxins, gibberellins, steroids, proteins, hydrophilic organic compounds, and analogs thereof. For example, in the case the linker substance is biotin, beads or a filter having avidin or streptavidin bound to the surface thereof can be used for the solid-phase support. Similarly, in the case the linker substance is glutathione, digoxigenin, digoxin, His tag, Flag tag or Myc tag, beads or a filter having antibody thereto bound to the surface thereof can be used for the solid-phase support.

There are no particular limitations on the solid-liquid separation treatment provided it employs a method that allows a solid-phase support present in solution to be recovered by separating from the liquid component, and a method can be used by suitably selecting from among known treatments used for solid-liquid separation treatment. For example, in the case the solid-phase support consists of particles such as beads, the solid-phase support may be allowed to precipitate by allowing a suspension containing the solid-phase support to stand undisturbed or by subjecting to centrifugal separation treatment followed by removal of the supernatant, or the solution may be filtered using filter paper or a filtration filter followed by recovering the solid-phase support remaining on the surface of the filter paper and the like. In addition, in the case the solid-phase support consists of magnetic beads, a magnet may be brought in close proximity to a container containing the solution to cause the solid-phase support to converge on the side of the container closest to the magnet followed by removing the supernatant. Furthermore, in the case the solid-phase support is a membrane or filter, non-degraded protease substrate can be separated and removed from the reaction solution by passing the reaction solution through the solid-phase support following incubation thereof.

The amount of the fluorescent substance derived from the degraded protease substrate can be measured by a typical fluorescence measurement method. For example, this method may consist of measuring fluorescence intensity emitted from all fluorescent molecules in a solution or measuring fluorescence intensity for each molecule.

The fluorescence intensity of a solution can be measured by an ordinary method using a fluorescence spectrophotometer such as a fluorescence plate reader. The fluorescence intensity of a solution is dependent on the amount of fluorescent substance in the solution. Therefore, by preliminarily preparing a calibration curve indicating the relationship between the concentration of a detection target in the form of the fluorescent substance and fluorescence intensity, for example, the amount of the fluorescent substance in the solution, namely the amount of the fluorescent substance derived from the degraded protease substrate, can be quantified.

Examples of methods used to measure fluorescence intensity for each molecule in a sample solution include fluorescence calibration spectroscopy (FCS) (see, for example, Japanese Unexamined Patent Application, First Publication No. 2005-98876), fluorescence intensity distribution analysis (FIDA) (see, for example, Japanese Patent No. 4023523), and scanning single-molecule counting (SSMC) (see, for example, Japanese Patent No. 05250152). In addition, fluorescence intensity of a single molecule may also be measured using the scanning single molecule detection analyzer described in Japanese Translation of PCT International Application Publication No. 2011-508219 or the single fluorescent particle detector disclosed in Japanese Unexamined Patent Application, First Publication No. 2012-73032. In the present invention, the fluorescent substance derived from the degraded protease substrate may be measured by the SSMC method since fluorescent substances can be detected quantitatively with high sensitivity from even smaller size samples.

For example, the number of molecules of a fluorescent substance derived from a degraded protease substrate present in a solution can be calculated by FCS by detecting fluctuations in the fluorescence intensity of molecules present in the area of the focal point of a confocal optical system followed by statistically analyzing those fluctuations.

In addition, the number of molecules of a fluorescent substance derived from a degraded protease substrate present in a solution can be calculated by FIDA by detecting fluctuations in the fluorescence intensity of molecules present in the area of the focal point of a confocal optical system followed by statistically analyzing those fluctuations.

In addition, the number of free molecules of a fluorescent substance derived from a degraded protease substrate present in a solution can be calculated by SSMC by using a confocal microscope or multiphoton microscope to move the location of the photodetection region of the optical system within the solution while detecting fluorescence emitted from the photodetection region.

Furthermore, FCS, FIDA and SSMC can be carried out according to ordinary methods using, for example, a known single molecule fluorescence analysis system such as the MF20 (Olympus).

In the case of measuring the amount of a fluorescent substance derived from a protease substrate using a fluorescent signal, although the measured fluorescent signal may be directly taken to be the amount of the fluorescent substance, in the case the measurement background level cannot be ignored, the value obtained by subtracting the background level may be used for the amount of the fluorescent substance.

Operation (a) and operation (b) are carried out before operation (c), and either operation may be carried out first or both operations may be carried out simultaneously. In addition, the duodenal fluid sample investigated for degradation activity on the chymotrypsin-specific substrate in operation (a) and the duodenal fluid sample investigated for degradation activity on the pepsin-specific substrate in operation (b) may be the same. For example, operation (a) may be carried out on a dispensed portion of one duodenal fluid sample and operation (b) may be carried out on another dispensed portion of that duodenal fluid sample, operation (b) may be carried out by adding the pepsin-specific substrate to the reaction liquid following investigation of degradation activity on the chymotrypsin-specific substrate in operation (a), or operation (a) may be carried out by adding the chymotrypsin-specific substrate to the reaction liquid following investigation of degradation activity on the pepsin-specific substrate in operation (b). In addition, the digestion reactions of operation (a) and operation (b) may be carried out simultaneously by adding the chymotrypsin-specific substrate and pepsin-specific substrate to a single duodenal fluid sample, followed by sequentially measuring the amount of degradation product of the chymotrypsin-specific substrate and amount of degradation product of the pepsin-specific substrate following the reaction (after incubating the reaction liquid).

In the case of labeling the chymotrypsin-specific substrate and pepsin-specific substrate with a fluorescent substance, and measuring the amount of degradation product of the chymotrypsin-specific substrate and amount of degradation product of the pepsin-specific substrate based on the fluorescent substance used to label each protease substrate, the fluorescent substances used to label both protease substrates have mutually different fluorescence properties. Here, having different fluorescence properties means that the wavelengths of fluorescent light emitted when irradiated with excitation light differ to the extent that they can be distinctly detected in the manner of FITC and rhodamine.

In operation (a) and operation (b), water or various buffers may be mixed into the reaction liquid when incubating a mixture obtained by mixing a duodenal fluid sample and protease substrate (reaction liquid). The water or buffer can be used to adjust the concentration or pH of the reaction liquid. A buffer can be used for the buffer by suitably selecting from among buffers commonly used in the art. Examples of buffers include phosphate buffers such as phosphate buffered saline (PBS, pH 7.4), Tris buffer, HEPES buffer and Hank's buffer.

In operation (a), a buffer having a pH of 7 to 9 may be mixed into the reaction liquid so as to reach the vicinity of the optimum pH of chymotrypsin. In addition, in operation (b), a buffer having a pH of 1 to 4 may be mixed into the reaction liquid so as to reach the vicinity of the optimum pH of pepsin.

Moreover, other substances may also be mixed into the reaction liquid obtained by mixing a duodenal fluid sample and protease substrates in operations (a) and (b) provided they do not inhibit the digestion reactions of chymotrypsin and pepsin. Examples of these other substances include surfactants and nuclease inhibitors.

In operations (a) and (b), there are no particular limitations on the amount of time spent incubating the reaction liquid obtained by mixing a duodenal fluid sample and protease substrates provided it is a sufficient amount of time for inducing the protease reactions, and can be suitably adjusted in consideration of such factors as the pH or amount of the reaction liquid or the incubation temperature. For example, an enzymatic reaction induced by chymotrypsin or pepsin can be carried out by incubating the reaction liquid for 5 minutes to 2 hours. In addition, the incubation temperature is only required to be a temperature that allows the protease reactions to proceed, and may be room temperature (1° C. to 30° C.) or in the vicinity of animal body temperature (30° C. to 38° C.). In addition, incubation may be carried out under constant temperature conditions or may be carried out without controlling temperature.

In the case of carrying out the method for evaluating suitability according to the present invention on a plurality of duodenal fluid samples, or in the case of independently carrying out the method for evaluating suitability according to the present invention and then comparing with the evaluation results of a different duodenal fluid sample that has been evaluated or is to be evaluated, the composition of the incubated reaction liquid along with the incubation time and temperature may be subjected to the same conditions between measurement samples since this makes it possible to prevent variations between measurement samples.

Following operations (a) and (b), sample suitability of the duodenal fluid sample used for measurement is evaluated in operation (c). A duodenal fluid sample in which degradation activity on the chymotrypsin-specific substrate is high and degradation activity on the pepsin-specific substrate is low, is evaluated as having high sample suitability. A duodenal fluid sample, in which the amount of degradation product of the chymotrypsin-specific substrate is high and the amount of degradation product of the pepsin-specific substrate is equal to or below the measurement limit, also has the highest sample suitability. In addition, a duodenal fluid sample in which, degradation activity on the chymotrypsin-specific substrate is low and degradation activity on the pepsin-specific substrate is high is evaluated as having low sample suitability. In the case of two or more duodenal fluid samples in which degradation activity on the chymotrypsin-specific substrates is roughly equal, the sample in which degradation activity on the pepsin-specific substrate is lower is evaluated as having higher sample suitability. In other words, although a duodenal fluid sample, in which degradation activity on the chymotrypsin-specific substrate is high but degradation activity on the pepsin-specific substrate is also high, has high sample suitability, it is evaluated as having lower sample suitability than a duodenal fluid sample in which degradation activity on the chymotrypsin-specific substrate is high and degradation activity on the pepsin-specific substrate is low. Although a duodenal fluid sample, in which degradation activity on the chymotrypsin-specific substrate low and degradation activity on the pepsin-specific substrate is also low, has low sample suitability, it is evaluated as having higher sample suitability than a duodenal fluid sample in which degradation activity on the chymotrypsin-specific substrate is low and degradation activity on the pepsin-specific substrate is high.

The degree of the degradation activity of two or more duodenal fluid samples, for which operation (a) was carried out under the same conditions, on the chymotrypsin-specific substrate can be determined by comparing measured values of the amounts of degradation product of the chymotrypsin-specific substrate. Similarly, the degree of the degradation activity of two or more duodenal fluid samples, for which operation (b) was carried out under the same conditions, on the pepsin-specific substrate can be determined by comparing measured values of the amounts of degradation product of the pepsin-specific substrate.

In addition, a duodenal fluid sample in which, after preliminarily determining a threshold value, the amount of degradation product of the chymotrypsin-specific substrate is higher than that prescribed threshold value can be evaluated as having high sample suitability, while a duodenal fluid sample in which the amount of that degradation product is below the prescribed threshold value can be evaluated as having low sample suitability. In addition, a duodenal fluid sample in which the amount of degradation product of the pepsin-specific substrate is below a prescribed threshold value can be evaluated as having high sample suitability, while a duodenal fluid sample in which the amount of that degradation product is higher than the prescribed threshold value can be evaluated as having low sample suitability.

In the method for evaluating sample suitability according to the present invention, degradation activity of a duodenal fluid sample on a chymotrypsin-specific substrate can be determined based on the chymotrypsin content of the duodenal fluid sample, and degradation activity of a duodenal fluid sample on a pepsin-specific substrate can be determined based on the pepsin content of the duodenal fluid sample. The chymotrypsin content and pepsin content of a duodenal fluid sample can be measured using an antigen-antibody reaction using antibody specific for chymotrypsin or pepsin, and a commercially available assay kit using the ELISA method can be used. For example, an example of a kit for measuring chymotrypsin concentration is the "Trypsin (E)(S)" kit (Kyowa Medex), while an example of a kit for measuring pepsin concentration is the "Human Pepsin PG ELISA Kit" (Cusabio).

A duodenal fluid sample targeted for evaluation in the method for evaluating suitably according to the present invention may be duodenal fluid collected from any location within the intestinal tract of the duodenum. The duodenal fluid sample may be duodenal fluid present in the second portion or third portion of the duodenum. Since the first portion of the duodenum is a site that connects directly from the pyloric region of the stomach, it has the possibility of being highly contaminated by gastric juice, and collection of duodenal fluid may be difficult from this site due to it being comparatively difficult to anchor the endoscope in order to collect duodenal fluid.

Furthermore, duodenal fluid can be collected according to ordinary methods. For example, duodenal fluid can be collected using a syringe, vacuum pump or other aspiration units connected to a liquid collection catheter provided in an endoscope. More specifically, the endoscope is inserted through the oral cavity to the duodenum and duodenal fluid present in the second portion and third portion of the duodenum is collected by aspiration using a catheter inserted therein after inserting with a forceps channel. For example, duodenal fluid that has accumulated in the digestive tract of the duodenum may be collected during the course of a gastroscopic procedure in the form of gastroduodenal endoscopy (upper endoscopy).

The composition of duodenal fluid varies considerably depending on the individual, and there are both large diurnal and daily variations even within the same subject. Moreover, the composition of duodenal fluid also varies depending on the location in the duodenum where it is collected. Consequently, even in the case of duodenal fluid samples collected on the same day from the same subject, pancreatic fluid content and gastric juice content vary considerably due to differences in the sites where the duodenal fluid samples were collected and the times at which they were collected. Therefore, it is preferable to respectively carry out operations (a) and (b) of the method for evaluating suitability according to the present invention on a plurality of duodenal fluid samples collected independently from various sites of the duodenum of the same subject, compare the measured degradation activities of each protease substrate, and use the sample having the highest sample suitability in actual testing for pancreatic fluid-derived components. By selecting a duodenal fluid sample having high sample suitability and using that sample in testing for pancreatic fluid-derived components, decreases in testing accuracy attributable to false negatives can be inhibited and testing efficiency can be enhanced.

Furthermore, in the present invention and present specification, pancreatic fluid-derived components refer to various biomolecules contained in pancreatic fluid such as proteins, nucleic acids, lipids or cells. The method for evaluating suitability according to the present invention may be used to evaluate the sample suitability of a duodenal fluid sample used in testing for pancreatic disease markers. Pancreatic disease markers are biomolecules for which concentration in pancreatic fluid increases significantly in patients suffering from pancreatic disease in comparison with patients not suffering from pancreatic disease. Furthermore, patients not suffering from pancreatic disease include not only healthy individuals, but also persons suffering from diseases other than pancreatic disease. In addition, examples of pancreatic diseases include pancreatic cancer, intraductal papillary mucinous neoplasm (IPMN), mucinous cystic neoplasm (MCN), serous cystic neoplasm (SCN), neuroendocrine tumor (NET), chronic pancreatitis (CP) and acute pancreatitis.

<Method for Practicing Collection of Duodenal Fluid Sample>

Duodenal fluid samples collected at a site near the pyloric region of the stomach are contaminated with large amounts of gastric juice, while those collected at a site close to the papillary region have a strong tendency to have a high content of pancreatic fluid. In other words, sample suitability of duodenal fluid samples is greatly affected by the collection site. The method for practicing collection of a duodenal fluid sample according to the present invention (to be referred to as the "method for practicing collection according to the present invention") is a method for practicing collection of duodenal fluid samples so as to be able to collect a simulated duodenal fluid sample having high sample suitability using a digestive tract simulator.

The digestive tract simulator used in the method for practicing collection according to the present invention simulates the structure of the digestive tract of an animal from the mouth to the duodenum, and is at least provided with a simulated mouth, a simulated esophagus, a simulated stomach injected with simulated gastric juice, and a simulated duodenum injected with simulated pancreatic fluid and simulated bile through a simulated papilla. The simulated duodenal fluid present in the simulated duodenum contains simulated gastric juice that gradually seeps in from the simulated stomach, and simulated pancreatic fluid and simulated bile that enter from the simulated papilla. The content of simulated gastric juice in the simulated duodenal fluid decreases moving away from the simulated stomach, while the content of simulated pancreatic fluid decreases moving away from the simulated papilla. The simulated gastric juice is a solution having a pH of 1 to 2 that contains pepsin, while the simulated pancreatic fluid is a solution having a pH of 7 to 9 that contains chymotrypsin. The simulated bile is a solution having a pH of 8 to 9 that contains bilirubin.

The digestive tract simulator used in the method for practicing collection according to the present invention simulates the structure of the digestive tract of an animal, and is only required to have the simulated duodenum filled with a liquid such that pepsin concentration decreases as distance from the simulated stomach increases, and chymotrypsin concentration decreases as distance from the simulated papilla increases. For example, a digestive tract simulator used to practice endoscopic procedures can also be suitably modified and used in the method for practicing collection according to the present invention.

In the method for practicing collection according to the present invention, the following operations (1) and (2) are carried out once or repeated two or more times:

(1) collecting a simulated duodenal fluid sample from one or two or more different sites of the simulated duodenum by inserting an endoscope equipped with an internal catheter for collecting body fluid from the simulated mouth to the simulated duodenum of the digestive tract simulator; and, (2) measuring each of the simulated duodenal fluid samples collected in (1) for degradation activity on the chymotrypsin-specific substrate and degradation activity on the pepsin-specific substrate, respectively.

Measurement of degradation activity of each of the simulated duodenal fluid samples in operation (2) on the chymotrypsin-specific substrate and pepsin-specific substrate can be carried out according to operations (a) and (b) in the method for evaluating suitability according to the present invention. A chymotrypsin-specific substrate having a chymotrypsin recognition site of the structure represented by the aforementioned general formula (1) is preferable for the chymotrypsin-specific substrate used in the method for practicing collection according to the present invention, a chymotrypsin-specific substrate having one or two labeling substances bound to a chymotrypsin recognition site of the structure represented by the aforementioned general formula (1) is more preferable, and a chymotrypsin-specific substrate having one or two fluorescent substances bound to a chymotrypsin recognition site of a structure represented by the aforementioned general formula (1) is even more preferable. A pepsin-specific substrate having a pepsin recognition site of the structure represented by the aforementioned general formula (2) is preferable for the pepsin-specific substrate used in the method for practicing collection according to the present invention, a pepsin-specific substrate having one or two labeling substances bound to a pepsin recognition site of the structure represented by the aforementioned general formula (2) is more preferable, and a pepsin-specific substrate having one or two fluorescent substances bound to a pepsin recognition site of a structure represented by the aforementioned general formula (2) is even more preferable.

In the method for practicing collection according to the present invention, collection is practiced by repeating the aforementioned operations (1) and (2) so that a duodenal fluid sample can be collected in which degradation activity on a chymotrypsin-specific substrate is higher than a prescribed threshold value and degradation activity on a pepsin-specific substrate is lower than a prescribed threshold value. The threshold values can be determined based on degradation activity on the chymotrypsin-specific substrate and degradation activity on the pepsin-specific substrate of simulated duodenal fluid collected from the vicinity of the papilla in the digestive tract simulator.

Although a digestive tract simulator is used in the method for practicing collection according to the present invention, the collection of a simulated duodenal fluid sample having high sample suitability can also be practiced using a live animal. The animal is only required to be an animal from which a duodenal fluid sample can be collected by inserting an endoscope equipped with an internal catheter for collecting body fluid, and examples thereof include humans, monkeys, cows, horses and sheep.

In the case of using a live animal, after having first inserted an esophagogastroduodenoscope from the mouth of the test animal until it reaches the duodenum, a catheter for collecting body fluid is inserted from the forceps opening, duodenal fluid samples are collected at a plurality of locations in the duodenum ranging from the vicinity of the pyloric region of the stomach to the papillary region, and degradation activity on a chymotrypsin-specific substrate and degradation activity on a pepsin-specific substrate of the collected duodenal fluid sample are measured. A duodenal fluid sample among the collected duodenal fluid samples, in which the degradation activity on the chymotrypsin-specific substrate is high while the degradation activity on the pepsin-specific substrate is low, is determined to have high sample suitability. Next, an endoscope is inserted into a test animal until it reaches the duodenum, a catheter for collecting body fluid is inserted from the forceps opening, and collection is practiced repeatedly so as to be able to collect a duodenal fluid sample having high sample suitability. Practice can be carried out in the same manner as operations (1) and (2) in the method for practicing collection according to the present invention.

EXAMPLES

Although the following provides a more detailed explanation of the present invention by indicating examples thereof, the present invention is not limited to the following examples.

Example 1

Sample suitability was evaluated according to the method for evaluating suitability according to the present invention for 10 duodenal fluid samples (Specimens A to J) independently collected from various sites in the duodenum of a single subject.

A compound obtained by linking a fluorescent substance in the form of CFRed590 (Cal Fluor Red 590 (ex: 569 nm, em: 591 nm)) and a quenching substance in the form of BHQ2C by a structure represented by the aforementioned general formula (1) was used as a chymotrypsin-specific substrate, and a compound obtained by linking a fluorescent substance in the form of Nma and a quenching substance in the form of Dnp by a structure represented by the aforementioned general formula (2) was used as a pepsin-specific substrate. More specifically, a compound represented by general formula (1a) was used for the chymotrypsin-specific substrate, and a compound represented by general formula (2a) was used for the pepsin-specific substrate.

[Chemical Formula 7]

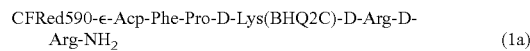

$$\text{CFRed590-}\epsilon\text{-Acp-Phe-Pro-D-Lys(BHQ2C)-D-Arg-D-Arg-NH}_2 \quad (1a)$$

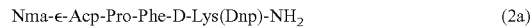

$$\text{Nma-}\epsilon\text{-Acp-Pro-Phe-D-Lys(Dnp)-NH}_2 \quad (2a)$$

Degradation activity on the chymotrypsin-specific substrate and pepsin-specific substrate was investigated for each of the collected duodenal fluid samples. More specifically, the chymotrypsin-specific substrate and pepsin-specific substrate were mixed with 50 μL of duodenal fluid sample in each well of a 96-well plate so that the final concentration of the chymotrypsin-specific substrate was 10 μM and the final concentration of the pepsin-specific substrate was 50 μM, followed by preparing a reaction liquid having a final volume 100 μL with Tris buffer (10 mM Tris-HCl, pH=8.5) or hydrochloric acid (10 mM HCl, pH=2.0). In addition, a specimen using 1 mg/mL pancreatin solution (Wako Pure Chemical Industries) instead of duodenal fluid sample was used as positive control for the chymotrypsin-specific substrate, a specimen using simulated gastric juice (Japanese Pharmacopoeia dissolution test, first liquid: aqueous solution having pH of 1.2 and containing 2 g of sodium chloride and 7 mL of hydrochloric acid per liter) instead of duodenal fluid sample was used as positive control for the pepsin-specific substrate, a specimen prepared to a final volume of 100 μL with Tris buffer without adding duodenal fluid sample was used as a negative control for the chymotrypsin-specific substrate, and a specimen prepared to a final volume of 100 μL with hydrochloric acid without adding duodenal fluid sample was used as a negative control for the pepsin-specific substrate.

After allowing the 96-well plate to react for 10 minutes at 37° C., the plate was placed on a plate reader followed by measuring fluorescence intensity having an excitation wavelength of 569 nm and fluorescence wavelength of 591 nm (Ex/Em=569/591), and fluorescence intensity having an excitation wavelength of 340 nm and fluorescence wavelength of 440 nm (Ex/Em=340/440), for the reaction liquids in each well.

The results of measuring fluorescence intensity of each duodenal fluid sample are shown in Table 1. Fluorescence intensity (Ex/Em=569/591) represents the amount of degradation product of the chymotrypsin-specific substrate, while fluorescence intensity (Ex/Em=340/440) represents the amount of degradation product of the pepsin-specific substrate. In Table 1, "NC" indicates the negative control while "PC" indicates the positive control. In addition, "Fluorescence intensity (Ex/Em=569/591)" indicates the intensity of fluorescence generated by degradation of the chymotrypsin-specific substrate, while "Fluorescence intensity (Ex/Em=340/440)" indicates the intensity of fluorescence generated by the degradation of the pepsin-specific substrate.

TABLE 1

| Duodenal fluid Sample | Fluorescence intensity. (Ex/Em = 569/591) | Fluorescence intensity (Ex/Em = 340/440) |
|---|---|---|
| Specimen A | 142.2 | 60.26 |
| Specimen B | 132.4 | 41.98 |
| Specimen C | 152.6 | 39.49 |
| Specimen D | 173.8 | 46.09 |
| Specimen E | 140.6 | 29.86 |
| Specimen F | 160.1 | 21 |
| Specimen G | 156.8 | 21.9 |
| Specimen H | 134.71 | 32.5 |
| Specimen I | 173.55 | 83.28 |

TABLE 1-continued

| Duodenal fluid Sample | Fluorescence intensity. (Ex/Em = 569/591) | Fluorescence intensity (Ex/Em = 340/440) |
|---|---|---|
| Specimen J | 98.14 | 127.23 |
| NC | 15.81 | 1.429 |
| PC | 804.4 | 218.5 |

As a result, chymotrypsin activity and pepsin activity were confirmed in all 10 types of the specimens. Fluorescence intensity (Ex/Em=569/591) was less than 100 for Specimen J only, while fluorescence intensity (Ex/Em=340/440) exceeded 50 for Specimens A, I and J only. In other words, although chymotrypsin activity was low for Specimen J, it was high for the other specimens. In addition, although pepsin activity was high for Specimens A, I and J, it was low for the other specimens. The degrees of chymotrypsin activity and pepsin activity of each specimen along with the results of evaluating suitability of the duodenal fluid samples for use as a sample for detecting pancreatic fluid-derived components based thereon are shown in Table 2. In Table 2, "○" indicates that the duodenal fluid sample has high suitability as a sample for detecting pancreatic fluid-derived components, "Δ" indicates somewhat high sample suitability, and "X" indicates low sample suitability. On the basis of these results, Specimens B, C, D, E, F, G and H were evaluated as duodenal fluid samples having high sample suitability as samples for detecting pancreatic fluid-derived components.

TABLE 2

| | | Chymotrypsin activity | |
|---|---|---|---|
| | | High | Low |
| Pepsin activity | High | Δ Specimens A, I | X Specimen J |
| | Low | ○ Specimens B, C, D, E, F, G, H | Δ |

INDUSTRIAL APPLICABILITY

According to the method for evaluating suitability according to the present invention, the sample suitability of a duodenal fluid sample can be evaluated, samples for use in testing can be screened, and the reliability of test results can be evaluated. In addition, according to the method for practicing collection according to the present invention, the skills of a person engaged in the collection of duodenal fluid samples can be improved to enable collection of duodenal fluid samples having sample suitability. Namely, the invention according to the present invention makes it possible to improve testing performance by curtailing waste associated with sample collection and testing, and reducing the occurrence of false negatives in the detection of pancreatic fluid-derived components, and can be used in fields involving the analysis of pancreatic disease markers and other pancreatic fluid-derived components, and particularly in fields such as clinical testing.

The invention claimed is:
1. A method for evaluating a suitability of a duodenal fluid sample as a sample for detecting pancreatic fluid-derived components, comprising:
(a) mixing a duodenal fluid sample with a chymotrypsin-specific substrate and measuring an amount of degradation of the chymotrypsin-specific substrate by the duodenal fluid sample, the chymotrypsin-specific substrate having a cleavage site for chymotrypsin represented by the following general formula (1):

$$—(Y^1)\, n^1\text{-}\,(X^1)\text{-Pro-}(Y^2)\, n^2\text{-} \qquad (1)$$

wherein, $Y^1$ and $Y^2$ respectively and independently represent an amino acid residue or $—CH_2—NH—$, $X^1$ represents Phe, Trp or Tyr, and $n^1$ and $n^2$ respectively and independently represent an integer of 1 to 10,
(b) mixing the duodenal fluid sample with a pepsin-specific substrate and measuring an amount of degradation of the pepsin-specific substrate by the duodenal fluid sample, the pepsin-specific substrate having a cleavage site for pepsin represented by the following general formula (2):

$$—(Y^3)n^3\text{-Pro-}(X^2)—(Y^4)n^4\text{-} \qquad (2)$$

wherein, $Y^3$ and $Y^4$ respectively and independently represent an amino acid residue or $—CH_2—NH—$, $X^2$ represents Phe, Trp or Tyr, and $n^3$ and $n^4$ respectively and independently represent an integer of 1 to 10, and
(c) evaluating that the duodenal fluid sample is suitable as a sample for detecting pancreatic fluid-derived components if the amount of degradation of the chymotrypsin-specific substrate by the duodenal fluid sample is higher than a first prescribed threshold and the amount of degradation of the pepsin-specific substrate by the duodenal fluid sample is lower than a second prescribed threshold, as being suitable as a sample for detecting pancreatic fluid-derived components.

2. The method for evaluating the suitability of a duodenal fluid sample as a sample for detecting pancreatic fluid-derived components according to claim 1, wherein the chymotrypsin-specific substrate and the pepsin-specific substrate are labeled with the same or different labeling substances.

3. The method for evaluating the suitability of a duodenal fluid sample as a sample for detecting pancreatic fluid-derived components according to claim 2, wherein the amount of degradation of the chymotrypsin-specific substrate and the amount of the pepsin-specific substrate are determined by using the labeling substances as an indicator.

4. The method for evaluating the suitability of a duodenal fluid sample as a sample for detecting pancreatic fluid-derived components according to claim 2, wherein the labeling substance is a fluorescent substance.

5. The method for evaluating the suitability of a duodenal fluid sample as a sample for detecting pancreatic fluid-derived components according to claim 1, wherein the steps (a) and (b) are respectively carried out on a plurality of duodenal fluid samples collected from two or more different sites of the digestive tract of the same subject, and the step (c) further comprises:
(c') evaluating a duodenal fluid sample among the plurality of duodenal fluid samples, in which an amount of degradation of the chymotrypsin-specific substrate is high and an amount of degradation of the pepsin-specific substrate is low, as being suitable as a sample for detecting pancreatic fluid-derived components.

6. The method for evaluating the suitability of a duodenal fluid sample as a sample for detecting pancreatic fluid-derived components according to claim 1, wherein the first prescribed threshold is a first value, the first value is a fluorescence intensity of the sample at wavelength 569 nm divided by a fluorescence intensity of the sample at 591 nm, wherein the first value is greater than 100.

7. The method for evaluating the suitability of a duodenal fluid sample as a sample for detecting pancreatic fluid-derived components according to claim 1, wherein the second prescribed threshold is a second value, the second value is a fluorescence intensity of the sample at wavelength 340 nm divided by a fluorescence intensity of the sample at 440 nm, wherein the second value is less than 50.

8. The method for evaluating the suitability of a duodenal fluid sample as a sample for detecting pancreatic fluid-derived components according to claim 1, wherein the first prescribed threshold is a first value, the first value is a fluorescence intensity of the sample at wavelength 569 nm divided by a fluorescence intensity of the sample at 591 nm, wherein the first value is greater than 100 and wherein the second prescribed threshold is a second value, the second value is a fluorescence intensity of the sample at wavelength 340 nm divided by a fluorescence intensity of the sample at 440 nm, wherein the second value is less than 50.

* * * * *